United States Patent [19]

Marcune et al.

[11] Patent Number: 5,156,588
[45] Date of Patent: Oct. 20, 1992

[54] EXTERNAL FIXATION SYSTEM FOR THE NECK

[75] Inventors: Benjamin F. Marcune, Bethlehem, Pa.; Lisa A. G. Tweardy, Mt. Laurel, N.J.

[73] Assignee: The Jerome Group Inc., Mt. Laurel, N.J.

[21] Appl. No.: 647,228

[22] Filed: Jan. 4, 1991

[51] Int. Cl.$^5$ ............................................. A61F 5/08
[52] U.S. Cl. ............................. 602/17; 128/DIG. 23; 602/37; 602/18
[58] Field of Search ............... 128/75, 76 R, 87 B, 128/DIG. 23

[56] References Cited

U.S. PATENT DOCUMENTS

| | | | |
|---|---|---|---|
| 2,820,455 | 1/1958 | Hall | 128/87 B |
| 3,604,412 | 9/1971 | Gardner | 128/75 |
| 3,654,923 | 4/1972 | Crutchfield . | |
| 3,669,102 | 6/1972 | Harris | 128/87 B X |
| 3,923,046 | 12/1975 | Heifetz . | |
| 4,360,028 | 11/1982 | Barbier . | |
| 4,397,307 | 8/1983 | Keller | 128/76 R |
| 4,444,179 | 4/1984 | Trippi . | |
| 4,612,930 | 9/1986 | Bremer . | |
| 4,667,660 | 5/1987 | Eingorn | 128/75 |
| 4,735,196 | 4/1988 | Krag et al. | 128/75 X |
| 5,010,881 | 4/1991 | Boudreau et al. | 128/87 B X |
| 5,062,415 | 11/1991 | Weatherby et al. | 128/87 B X |
| 5,063,920 | 11/1991 | Moore | 128/87 B |

FOREIGN PATENT DOCUMENTS

| | | | |
|---|---|---|---|
| 3302078 | 7/1984 | Fed. Rep. of Germany | 128/75 |
| 140162 | 12/1960 | U.S.S.R. | 128/75 |
| 0633526 | 11/1978 | U.S.S.R. | 128/75 |
| 1489760 | 6/1989 | U.S.S.R. | 128/75 |
| 1503797 | 8/1989 | U.S.S.R. | 128/76 R |

OTHER PUBLICATIONS

"Low-Profile Halo Group by Ace Orthopedic Company"; The Journal of Bone & Joint Surgery, vol. 55A/4; Jun. 1973, p. 111.
Durr-Fillauer Medical, Inc. Advertisements dated prior to Jan. 4, 1991.
Kirschner Orthopedic Appliances Advertisements dated prior to Jan. 4, 1991.
Bremer Orthopedics Advertisements dated prior to Jan. 4, 1991.
Ace Medical Company Advertisements dated prior to Jan. 4, 1991.
Promotional Material from Levtech, 1986.
Advertisements from Progress Mankind Technology (PMT) Corporation from 1986–1988.

Primary Examiner—Robert Bahr
Assistant Examiner—Linda C. M. Dvorak
Attorney, Agent, or Firm—Ratner & Prestia

[57] ABSTRACT

A device is provided for maintaining the head of a patient in predetermined spatial relationship to the body of the patient. The device comprises an elliptical truncated member (halo) adapted to fit around the patient's head from front to back. The elliptical member, or open-backed halo includes a stiffening brim integrally associated with it at the front portion of the halo. The halo also includes a plurality of mounting holes and vibrational isolators for receiving skull pins to contact and grip the patient's head. The halo further includes, midway between the front and rear of the elliptical member two depressed segments which allow for positioning of skull tongs on the patient's head while the halo remains on the patient. The device also includes adjustable means for attaching the open-backed halo to a vest worn by the patient.

7 Claims, 5 Drawing Sheets

EXTERNAL FIXATION SYSTEM FOR THE NECK

FIELD OF THE INVENTION

This invention relates to a medical apparatus for securing a patient's head in a rigid spatial relationship to the patient's body, useful in the treatment of fractures of the cervical spine.

BACKGROUND OF THE INVENTION

There are applications in orthopedic surgery, neurosurgery, and other medical treatments and operative procedures where a patient's head must be engaged and held in a predetermined position with respect to the patient's body. Very often, during healing of injuries involving fracture or dislocation of the cervical spine, patient's head must be immobilized with respect to the patient's body in order to allow the fractured or dislocated bones to heal. For this purpose, halo traction units have been developed.

A halo traction unit comprises a halo, which rings the patient's head, a superstructure, and a vest, to which the superstructure is secured. The ring halo is held rigidly to the patient's head by "skull pins" which project through threaded holes in the halo and into the patient's skull. Thus the ring halo is held rigidly to the patient's head. The ring halo is then secured to the superstructure which in turn is secured to a vest which the patient wears on his or her chest. This structure maintains the head in a rigid, fixed relationship to the body.

While the patient's head is immobilized, it may be desirable to subject the patient to a magnetic resonance imaging machine (MRI, or NMR) or conventional x-rays, CAT scan, or other radiographic imaging tests. Therefore, it is desirable that the material for a halo be non-magnetic, and radio transparent, or at least that the material not interfere significantly with such tests.

When a patient initially enters a hospital directly from an accident scene, very often he or she will be strapped to a backboard or other head and neck immobilizing device. Based upon diagnostic results it may be desirable to attach a halo or skull tongs to provide traction and/or to immobilize the head and neck without moving the patient until the treatment has been applied. Many prior art halos are circular, and completely encircle the head of the patient. This makes impossible the application of the halo to the patient without removal of the patient from the backboard. Therefore, the patient's head must be moved or extended over the edge of the backboard or bed.

Recently, halos have been developed which have open backs, and which, therefore, allow application to the patient while the patient remains on a backboard or bed. However, due to the materials of construction and particular configurations of such open-backed halos, the open-backed halos are not extremely rigid. This instability is caused by removal of the back portion of the halo. As a result, the halo flexes when applied to and worn by the patient. This flexing results in movement of the skull pins against the skull and possible loosening of the skull pins. Such movement results in infections and other associated problems and should be eliminated. Preferably, one step toward elimination of these problems would be development of an open-backed halo with high rigidity.

Movement and loosening of skull pins is also caused by vibrations transmitted from the vest to the halo and patient's head through the superstructure and skull pins of the halo. The vibrations are caused simply by walking or other common movement. The transmission of these vibrations should also be reduced or eliminated to lessen the possibility of loosening of the skull pins.

If a patient is subjected to traction using skull tongs, prior art ring halos and open-backed halos require that the skull tongs be removed prior to application of the halo. It is undesirable to remove a patient from traction in this manner, and thus it would be preferable to apply a halo without removal of the skull tongs. This has heretofore been impossible.

Once a patient has been fitted with a halo, the halo is attached to a superstructure and vest worn by the patient, as previously explained. Generally, such attachment is accomplished by four vertical posts which run from the halo to a vest unit. Drawbacks with such a system include difficulty of adjusting of four separate posts to obtain even tension on the posts, and to obtain the correct position of the patient's head with respect to the patient's body. Further, such a unit is somewhat unnerving and distressing to patients. A superstructure which would provide simple adjustment without bulkiness would therefore be desirable.

SUMMARY OF THE INVENTION

The present invention comprises a device for maintaining the head of a patient in predetermined spatial relationship to the body of the patient. The device comprises an elliptical member (halo) adapted to fit around the patient's head from front to back. The elliptical member is truncated at the back (open-backed), and includes downwardly projecting segments adjacent the truncated portion. The elliptical member, or open-backed halo includes a stiffening brim integrally associated with it at the front portion of the halo. The halo also includes a plurality of mounting holes for receiving skull pins to contact and grip the patient's head. Further, midway between the front of the elliptical member (open-backed halo) and the rear of the elliptical member are located two depressed segments. Each depressed segment allows for positioning of skull tongs on the patient's head, thus allowing application of the halo while the skull tongs remain on the patient. The device also includes adjustable means for attaching the open-backed halo to a vest worn by the patient. The adjustable means comprises two elongated vertical height adjusters which attach to the depressed sections of the open-backed halo or elliptical member, and to a vertical support, which is then attached to a vest worn by the patient. This combination provides simple adjustment and positioning of the head of the patient. The skull pins of the present invention are equipped with vibrational isolators to reduce transmission of vibrations from the halo, vest, and superstructure to the skull pins, thereby reducing pin loosening and accompanying complications.

DETAILED DESCRIPTION OF THE DRAWINGS

Figure 1:
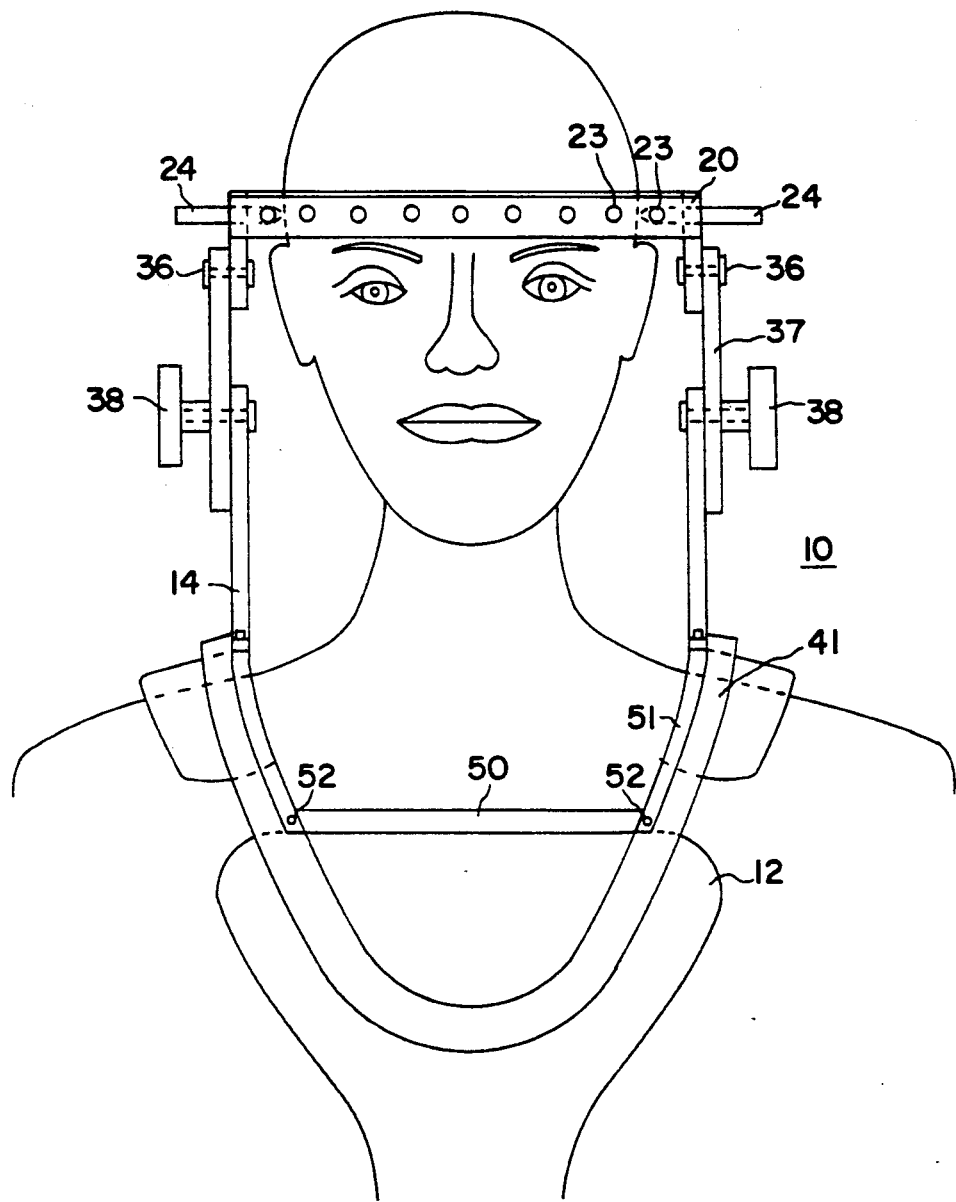
FIG. 1 is a front view of the device of the present invention when fitted to a wearer.

Referring now to FIG. 1, head immobilizing device 10 comprises generally halo, or elliptical member, 20, and means for rigidly attaching the halo to the patient's body, comprising generally a vest 12 and a superstructure 14. The component 20 of the present invention will be referred to here as a "halo" which is the term commonly used by those skilled in the art, or "elliptical member" which defines the component in terms of its shape. It should be understood that these terms are being used interchangeably.

Figure 2:
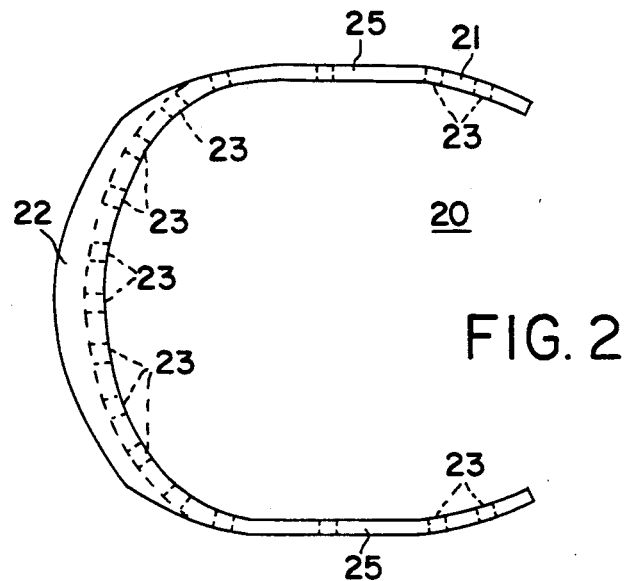
FIG. 2 is a top view of the halo of the device of the present invention.
Figure 3:
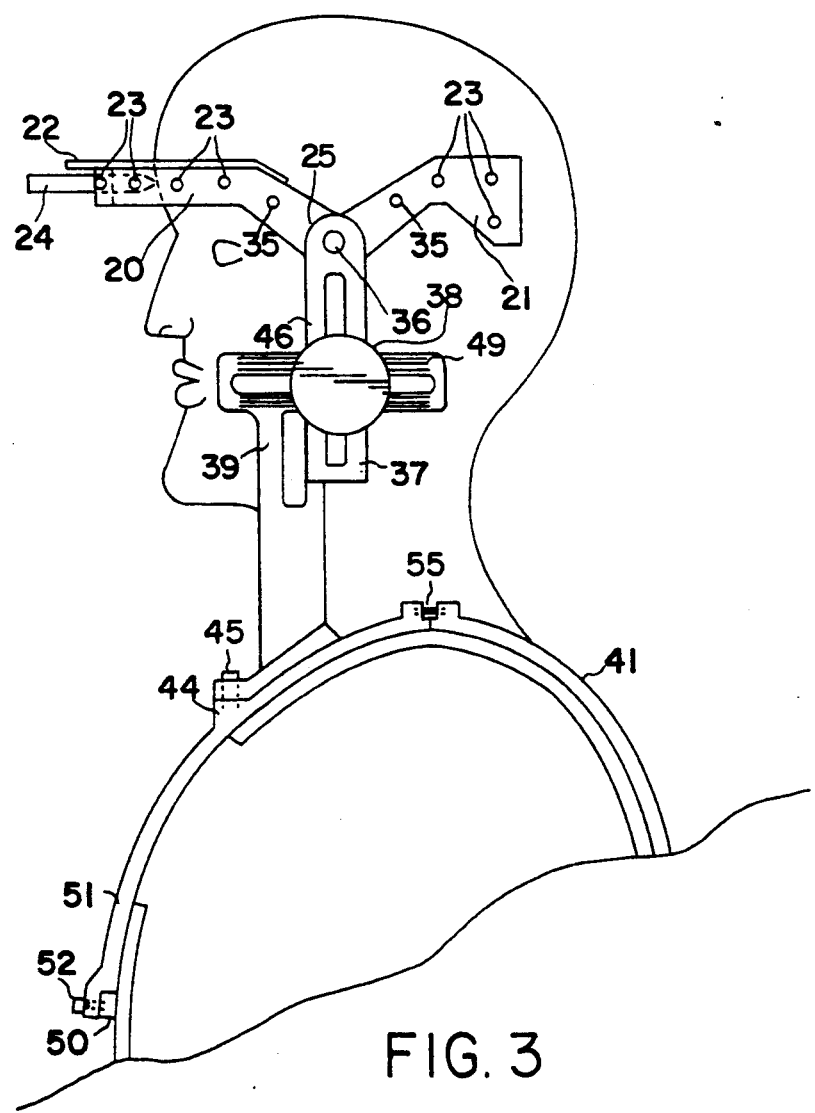
FIG. 3 is a side view of the device of the present invention when fitted to a wearer.

The particular configuration of the halo 20 can be more easily seen from FIGS. 2 and 3. Halo 20 is a truncated elliptical member as may be seen from FIG. 2. When applied to a patient, as shown in FIG. 3, the halo encircles the patient's head horizontally, just above the ears and eyebrows of the patient. This area may be referred to as the "equator" of the patient's head, or as a capital-distal plane. The halo is truncated, so the back thereof is removed and open. As used herein, the "back" or "front" of the halo refer to the portions of the halo at the posterior and anterior of the patient respectively when the halo is applied as shown in FIG. 3. The truncation allows the halo to be applied to a person secured to a backboard or lying supine in a bed, without removal of the patient's head from the backboard or bed surface. Adjacent the truncated section of the halo are two downwardly projecting segments 21, which extend out of the plane of the major portion of the halo. The extension of these sections allows one to obtain a more secure grip on the head of the patient by placing the skull pins below the capital-distal plane where optimum bone purchase is achieved. Of course, a halo in which these segments 21 were not extended could also be used, but the halo with segments 21 extended downwardly is preferred.

Figure 5:
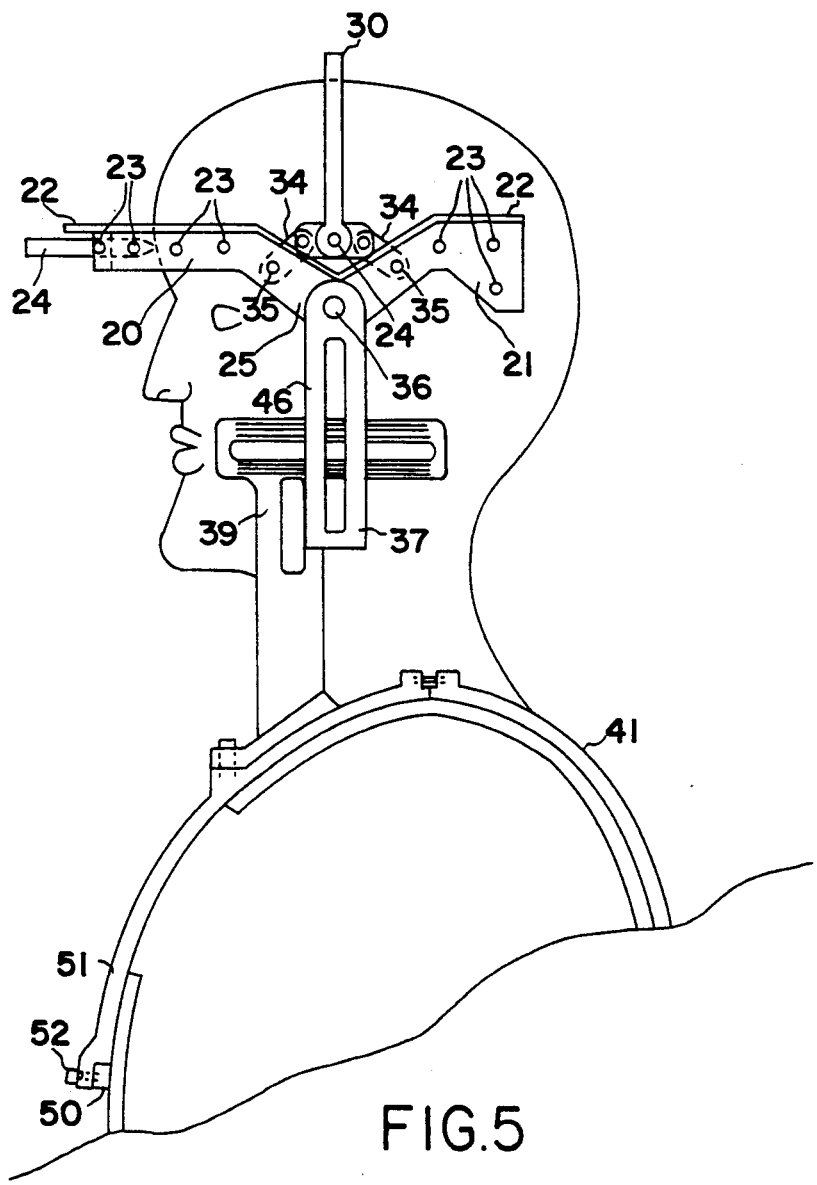
FIG. 5 is a side plan view of the device of the present invention when fitted to a wearer showing placement of skull tongs.

As previously mentioned, structural rigidity of halo 20 is a major concern in avoiding skull pin complications. Therefore halo 20 also includes a stiffening brim 22 integrally associated therewith. The brim is generally a flat, arcuate piece of material and may be made from the same material of construction as the remainder of the curved halo 20. Brim 22 may be made separately from the remainder of halo 20, in which case the brim should be welded, or permanently attached by other means to halo 20. If made separately, brim 22 can be made from a different material from halo 20. Brim 22 may also be made integrally with the remainder of halo 20 as a one-piece, molded or formed unit. The brim adds rigidity and flexural stability to halo 20, and this allows the integrity of the ring to be broken and the skull pins to be securely fastened to the patient's head without movement or flexing of halo 20, which would otherwise cause the skull pins to move, leading to infection and associated problems. Brim 22 is located in the front of halo 20, but may also extend over the entire length of halo 20 as shown in FIG. 5.

Halo 20 is provided with a plurality of holes 23 which allow for the use of skull pins 24. The manner for attaching skull pins 24 to halo 20 may be more clearly seen from FIG. 6.

As previously mentioned, it is desirable to reduce transmission of vibrations from halo 20 and the superstructure and vest, to the skull pins 24. Such vibrations may cause loosening of skull pins 24. This leads to movement of the skull pins on the patient's head. This can cause the patient's skull to wear down in those places where the skull pins are located. Then, even after tightening, skull pins 24 cannot grip the patient's head securely. Further, movement of skull pins 24 can lead to infection where the pins enter the patient's skin.

Figure 6:
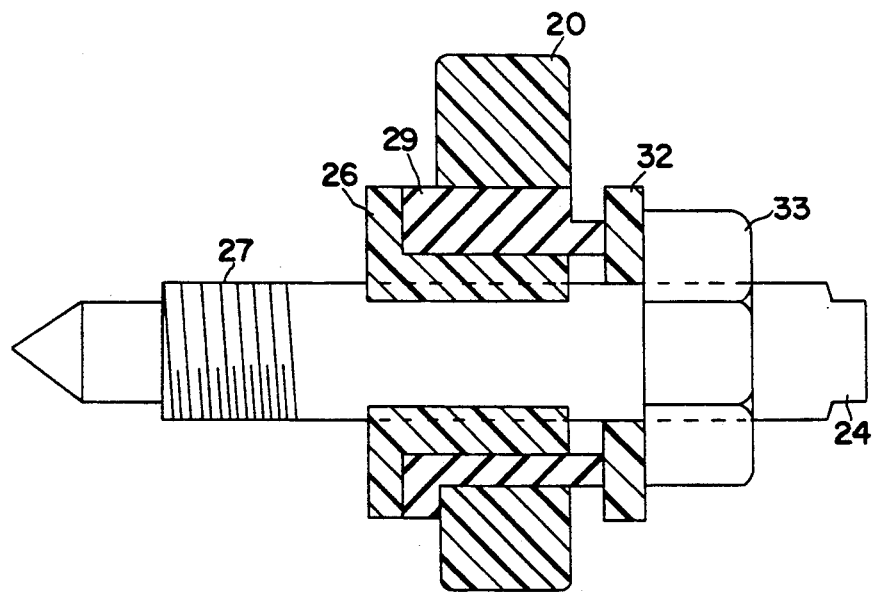
FIG. 6 is a cross-sectional view of a skull pin and accompanying vibrational isolator of the present invention, taken along line 6—6 of FIG. 7.
Figure 7:
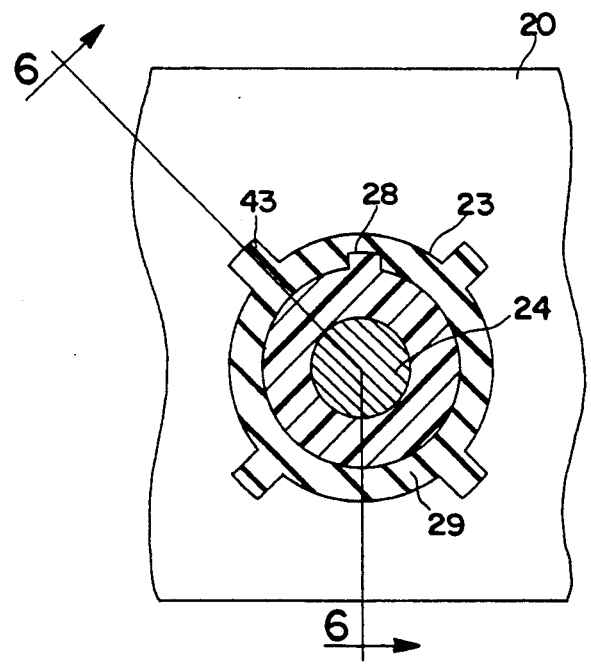
FIG. 7 is a cross-sectional view of a skull pin and accompanying vibrational isolator of the present invention.

FIG. 6 shows skull pin 24 which screws into molded nut 26 thru threads 27. Molded nut 26 is held in rubber isolation mount 29 which, in turn, is fitted in one of the mounting holes 23. Molded nut 26 has a key 28 to prevent rotation of nut 26 with respect to isolation mount 29. Isolation mount 29 also includes keys 43 to prevent rotation with respect to halo 20. Isolation mount 29 may be made from any suitable elastomeric material and is preferably made from hard rubber which has a high durometer. Once skull pin 24 has been secured in molded nut 26, fiber washer 32 and nut 33 lock the skull pin in the predetermined position and lock the entire vibration isolating assembly to halo 20 through mounting hole 23. Molded nut 26, fiber washer 32, and nut 33 may all be made from the same material, such as a polymeric resin, a carbon or glass fiber reinforced resin, or a non-magnetic metal alloy. Preferably, a long glass fiber reinforced nylon composite such as Verton from LNP Engineering Plastics in Exton, Pennsylvania may be used for halo 20. Like halo 20, molded nut 26, fiber washer 32, and nut 33 should not be made from a magnetic material so that the patient can be subjected to magnetic resonance imaging or similar diagnostic procedures. A polyether sulfone also from LNP Engineering Plastics in Exton, Pennsylvania is recommended. The entire vibration isolation assembly, comprising molded nut 26, rubber isolation mount 29, fiber washer 32, and nut 33, is held in halo 20 through mounting hole 23 and serves to hold halo 20 rigidly to the patient's head while preventing transmission of vibrations from the patient's vest, superstructure, and halo, to skull pins 24. Skull pins 24 are therefore less likely to loosen or move, and associated complications are reduced.

As shown in FIGS. 2 through 5 halo 20 also includes depressed segments 25 on either side thereof, located approximately midway between the front of the halo where the brim is located and the back of the halo which has been truncated. The depressed segments 25 provide a number of advantages as may be seen from FIGS. 4 and 5, depressed segments 25 allow skull tongs 30 to remain in position on the patient's head while halo 20 is applied. Generally, skull tongs are used for applying traction to a patient in the supine position. The skull tongs are generally applied on the equatorial (or capital distal) plane of the patient's head. As previously explained, this is the same position in which a halo is normally applied. Therefore prior art halos could not be applied to a patient when skull tongs were in place. This meant that a patient had to be removed from traction to apply the halo. Further, with a prior art halo in place, the skull tongs could not be reapplied and the patient could not be placed under traction except that supplied to the halo ring itself by some external means or by the vest, superstructure, and halo.

Depressed segments 25 allow for attachment of skull tongs 30 while halo 20 is secured to the patient, or alternatively, allows halo 20 to be positioned while skull tongs 30 remain in place. The open back of halo 20 enables the halo to be manipulated around skull tongs 30 or a cable attached thereto for supplying traction. The patient can therefore be subjected to traction without a vest while halo 20 is in place. Skull tongs 30 can be secured directly to halo 20, as may be seen in FIG. 5. Skull tongs 30 are equipped with flanges 34. The flanges attach to the skull tongs 30 and to holes 35 in halo 20. These holes may be threaded to accommodate a fastener or a nut may be used with the fastener. Depressed segment 25 allows proper placement of the skull tongs 30 with skull pin 24 in the equatorial plane of the patient's head.

Figure 4:
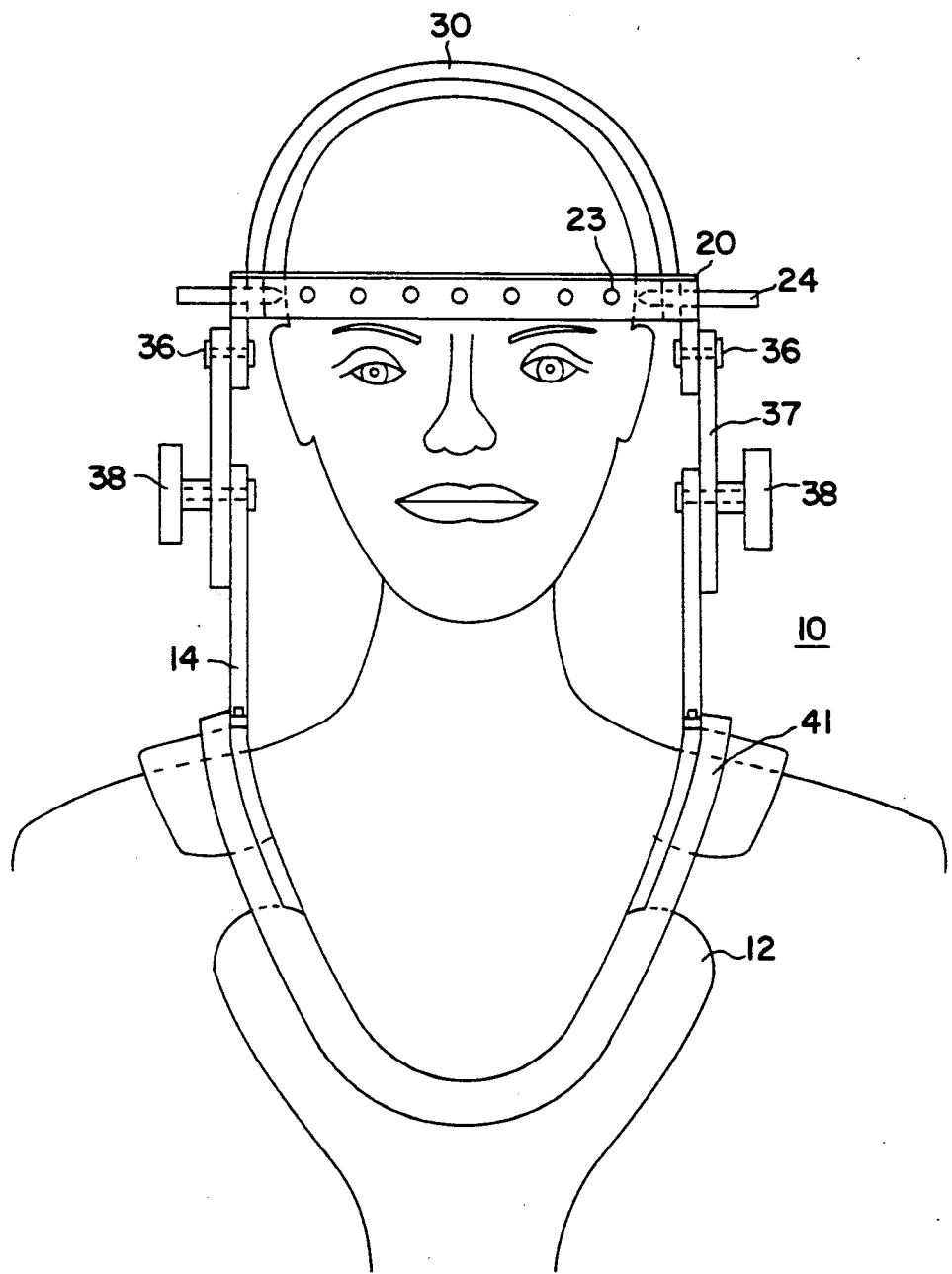
FIG. 4 is a front view of the device of the present invention when fitted to a wearer showing placement of skull tongs.
Figure 8:
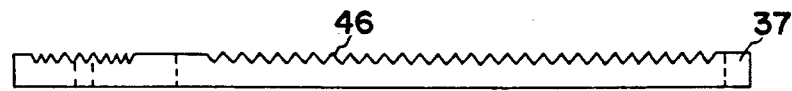
FIG. 8 is a side view of a vertical height adjuster of the present invention.

Depressed segments 25 also provide for attachment of halo 20 to supporting superstructure 14 as shown in FIGS. 3-5. Halo 20 attaches to vertical height adjuster 37 through lock screw 36. Vertical height adjuster is in turn secured to vertical support 39. Vertical height adjuster 37 and vertical support 39 are equipped with V-grooves 46 and 49 respectively. Vertical height adjuster 37 and vertical support 39 are arranged such that the V-grooves interlock and thus hold the halo securely. Vertical height adjuster 37 can be more easily seen in FIG. 8. V-grooves 46 are adapted to interlock with V-grooves 49 on vertical support 39.

Vertical height adjuster 37 also has V-grooves which interlock with V-grooves on halo 20. These V-grooves on vertical height adjuster 37 and halo 20 cannot be seen from the figures since superstructure 14 is shown assembled mounted on a patient. Vertical support 39 is attached to over shoulder bar 41, by means of flange 44 on over shoulder bar 41. Vertical support 39 and flange 44 each have V-grooves which interlock. By loosening lock screw 45 rotation about the screw is possible to obtain rotational adjustment of the halo 20. As may be seen from FIGS. 3 and 5, over the shoulder bars are hinged at ball and socket joint 55 to allow rotation around the patient, so that they may be applied while a patient is supine in bed. Vertical height adjuster 37 and vertical support 39 with interlocking V-grooves are held securely together by means of lock knob 38. Lock knob is knurled and can be hand tightened and adjusted to facilitate adjustment of the height of superstructure 14 and halo 20. Lock knob 38 also includes an allen-type (hex socket) locking screw for locking the knob when suitable adjustments have been made. All parts of superstructure 14 are preferably made from the same or similar material to that used for halo 20 since superstructure should also be nonmagnetic and should not allow artifact during diagnostic imaging.

Lateral adjustment of halo 20 and superstructure 14 may be made by means of lateral lock nut 52, as shown in FIGS. 1, 3, and 5. Chest bar 50 connects the two sides of superstructure 14 and front brace 51 connects thereto. Front brace 51 comprises the front portion of over shoulder bar 41. Front brace 51 has V-grooves where it connects to chest bar 50. This allows simple adjustment and securing of the superstructure.

It is understood that various other modifications will be apparent to one skilled in the art without departing from the spirit and scope of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A device for maintaining the head of a patient in a predetermined spatial relationship to the body of the patient, and immobilizing the neck of the patient, said device comprising:

an elliptical member adapted to encircle the head of the patient from front to back, said elliptical member truncated at the back thereof, said elliptical member including downwardly projecting segments adjacent said truncation;

said elliptical member including a stiffening brim;

said elliptical member including a plurality of mounting holes for receiving skull pins, which pins contact the patient's head and hold said elliptical member to the patient's head; and means for rigidly attaching said elliptical member to the body of the patent.

2. A device for maintaining the head of a patient in a predetermined spatial relationship to the body of the patient, said device comprising:

an elliptical member including a plurality of mounting holes for receiving skull pins, which pins contact the patient's head and hold said elliptical member to the patient's head;

adjustable means for rigidly attaching said elliptical member to the body of the patient; and means for vibrationally isolating said skull pins from said elliptical member, said isolation means comprising:

a cylindrical elastomeric member having projecting keys for securing said elastomeric member in said mounting holes;

a first nut adapted to receive said skull pin and having projecting keys for securing said threaded member in said elastomeric member; and a second nut for locking said skull pin in said threaded member.

3. A device for maintaining the head of a patient in a predetermined spatial relationship to the body of the patient, said device comprising:

an elliptical member including a plurality of mounting holes for receiving skull pins, which pins contact the patient's head and hold said elliptical member to the patient's head;

said elliptical member having front and rear portions for positioning toward the front and rear of the patient's head respectively;

said elliptical member also including, midway between said front and back portions thereof, depressed segments adapted to permit contact of the patient's head by skull tongs on both sides of the patient's head and generally in the plane of said elliptical member when said elliptical member is held to the patient's head by said skull pins; and adjustable means for rigidly attaching said elliptical member to the body of the patient.

4. The device of claim 3, further including a stiffening member located in the front of said elliptical member and extending between said depressed segments.

5. The device of claim 4, further including means for vibrationally isolating said skull pins from said elliptical member.

6. The device of claim 3, further including means for vibrationally isolating said skull pins from said elliptical member.

7. A device for maintaining the head of a patient in a predetermined spatial relationship to the body of the patient, said device comprising:

an elliptical member adapted to encircle the patient's head from front to back, said elliptical member truncated at the back thereof, said elliptical member including downwardly projecting segments adjacent said truncation;

said elliptical member including a stiffening brim integrally associated therewith at the front thereof;

said elliptical member including a plurality of mounting holes for receiving skull pins, which pins contact the patient's head and hold said elliptical member to the patient's head;

said elliptical member also including, midway between the front and back thereof, depressed segments adapted to permit contact of the patient's head by skull tongs on both sides of the patient's head and generally in the plane of said elliptical member when said elliptical member is held to the patient's head by said skull pins;

adjustable means for rigidly attaching said elliptical member to the body of the patient, said adjustable means comprising:

an elongated vertical height adjuster, including V-grooves, for attachment to said depressed segments of said elliptical member; and a vertical support, including V-grooves, for attachment to said vertical height adjuster, wherein said vertical support V-grooves are adapted to interlock with said vertical height adjuster V-grooves; and means for vibrationally isolating said skull pins from said elliptical member, said isolation means comprising:

a cylindrical elastomeric member having projecting keys for securing said elastomeric member in said mounting holes;

a first nut adapted to receive said skull pin and having projecting keys for securing said threaded member in said elastomeric member; and a second nut for locking said skull pin in said threaded member.

* * * * *